US012605202B2

(12) United States Patent
Dando et al.

(10) Patent No.: US 12,605,202 B2
(45) Date of Patent: Apr. 21, 2026

(54) DEVICE AND ACCESSORIES FOR A PERCUTANEOUS ENDOSCOPIC ACCESS AND ABLATION SYSTEMS

(71) Applicant: AtriCure, Inc., Mason, OH (US)

(72) Inventors: Jeremy Dando, Plymouth, MN (US); Jason Quill, Forest Lake, MN (US); Ram Kumar, Corcoran, MN (US); Tamer Ibrahim, Danville, CA (US); Guy Vanney, Blaine, MN (US); Al Mclevish, Roseville, MN (US); Aaron Owens, Hopkins, MN (US)

(73) Assignee: AtriCure, Inc., Mason, OH (US)

( * ) Notice: Subject to any disclaimer, the term of this patent is extended or adjusted under 35 U.S.C. 154(b) by 42 days.

(21) Appl. No.: 18/773,970

(22) Filed: Jul. 16, 2024

(65) Prior Publication Data

US 2024/0366299 A1     Nov. 7, 2024

Related U.S. Application Data

(60) Division of application No. 16/925,772, filed on Jul. 10, 2020, now Pat. No. 12,059,200, which is a
(Continued)

(51) Int. Cl.
*A61B 18/14*     (2006.01)
*A61B 17/00*     (2006.01)
(Continued)

(52) U.S. Cl.
CPC .......... *A61B 18/1492* (2013.01); *A61B 34/20* (2016.02); *A61B 2017/00323* (2013.01); *A61B 2017/320069* (2017.08); *A61B 2018/00577* (2013.01); *A61B 2018/00839* (2013.01); *A61B 2018/0212* (2013.01);
(Continued)

(58) Field of Classification Search
CPC ................ A61B 14/1492; A61B 34/20; A61B 2034/105; A61B 2017/320069; A61B 18/24; A61B 2017/00323; A61B 2018/00577; A61B 2018/00839; A61B 2018/0212; A61B 2018/1435; A61B 2018/1861; A61B 2218/002; A61M 25/0082; A61M 25/0136; A61M 25/09
See application file for complete search history.

(56) References Cited

U.S. PATENT DOCUMENTS 5,605,543 A     2/1997  Swanson
6,074,351 A     6/2000  Houser et al.
(Continued)

FOREIGN PATENT DOCUMENTS

EP     3015064     5/2016
EP     3391928     10/2018
(Continued)

*Primary Examiner* — Linda C Dvorak
*Assistant Examiner* — Abigail Bock
(74) *Attorney, Agent, or Firm* — Levine Bagade Han LLP

(57)     ABSTRACT
Devices, systems, and methods for therapeutically treating tissue. The devices and methods are suitable for minimally invasive surgery or open surgical procedures. More particularly, methods and devices described herein permit accessing and/or treating areas of tissue with a therapeutic device.

9 Claims, 11 Drawing Sheets

Related U.S. Application Data continuation of application No. PCT/US2019/013074, filed on Jan. 10, 2019.

(60) Provisional application No. 62/615,912, filed on Jan. 10, 2018.

(51) Int. Cl.

| | |
|---|---|
| *A61B 17/32* | (2006.01) |
| *A61B 18/00* | (2006.01) |
| *A61B 18/02* | (2006.01) |
| *A61B 18/18* | (2006.01) |
| *A61B 18/24* | (2006.01) |
| *A61B 34/10* | (2016.01) |
| *A61B 34/20* | (2016.01) |
| *A61M 25/00* | (2006.01) |
| *A61M 25/01* | (2006.01) |
| *A61M 25/09* | (2006.01) |

(52) U.S. Cl.

CPC .................. *A61B 2018/1435* (2013.01); *A61B 2018/1861* (2013.01); *A61B 18/24* (2013.01); *A61B 2034/105* (2016.02); *A61B 2218/002* (2013.01); *A61M 25/0082* (2013.01); *A61M 25/0136* (2013.01); *A61M 25/09* (2013.01)

(56) References Cited

U.S. PATENT DOCUMENTS

| | | | |
|---|---|---|---|
| 6,893,442 | B2 | 5/2005 | Whayne |
| 7,063,698 | B2 | 6/2006 | Whayne et al. |
| 7,410,487 | B2 | 8/2008 | Whayne |
| 7,572,257 | B2 | 8/2009 | Whayne et al. |
| 7,758,578 | B2 | 7/2010 | Whayne et al. |
| 7,780,661 | B2 | 8/2010 | Whayne et al. |
| 7,803,155 | B2 | 9/2010 | Whayne et al. |
| 8,034,053 | B2 | 10/2011 | Whayne et al. |
| 8,858,552 | B2 | 10/2014 | Whayne et al. |
| 9,603,657 | B2 | 3/2017 | Whayne |
| 9,603,658 | B2 | 3/2017 | Whayne et al. |
| 2005/0070844 | A1 | 3/2005 | Chow et al. |
| 2008/0103355 | A1 | 5/2008 | Boyden et al. |
| 2009/0024089 | A1* | 1/2009 | Levine .................. A61M 29/00 606/191 |
| 2010/0312056 | A1 | 12/2010 | Galperin et al. |
| 2011/0054465 | A1 | 3/2011 | Werneth et al. |
| 2013/0345694 | A1 | 12/2013 | Swanson |
| 2014/0155885 | A1 | 6/2014 | Ibrahim et al. |
| 2014/0358140 | A1 | 12/2014 | Emmons et al. |
| 2016/0038769 | A1 | 2/2016 | Sullivan et al. |
| 2016/0113656 | A1* | 4/2016 | Hughett ............... A61B 17/083 606/142 |
| 2016/0220306 | A1 | 8/2016 | Whayne et al. |
| 2016/0242788 | A1* | 8/2016 | Privitera ........... A61B 17/0218 |
| 2017/0231517 | A1 | 8/2017 | Severino |
| 2018/0028225 | A1 | 2/2018 | Whayne et al. |
| 2020/0337766 | A1 | 10/2020 | Dando et al. |

FOREIGN PATENT DOCUMENTS

| | | |
|---|---|---|
| JP | 2006-500169 | 1/2006 |
| JP | 2013-525016 | 6/2013 |
| JP | 2014-529429 | 11/2014 |
| WO | WO 2013/016722 | 1/2013 |
| WO | WO 2019/140105 | 7/2019 |

* cited by examiner

FIG. 5B                    FIG. 5C

DEVICE AND ACCESSORIES FOR A PERCUTANEOUS ENDOSCOPIC ACCESS AND ABLATION SYSTEMS

CROSS-REFERENCE TO RELATED APPLICATIONS

This application is a divisional of U.S. patent application Ser. No. 16/925,772, which is a continuation of International Patent Application No. PCT/US2019/013074 filed Jan. 10, 2019, which claims priority to U.S. Provisional Patent Application No. 62/615,912 filed Jan. 10, 2018, which are incorporated by reference herein in their entireties.

FIELD OF THE INVENTION

Devices, systems, and methods for therapeutically treating tissue. The devices and methods are suitable for minimally invasive surgery or open surgical procedures. More particularly, methods and devices described herein permit accessing and/or treating areas of tissue with a therapeutic device.

BACKGROUND OF THE INVENTION

Atrial fibrillation surgery requires creation of an ablation or coagulation lesion in atrial tissue. Typically, a physician creates a lesion using energy (including but not limited to cryogenic, radiofrequency, D.C., microwave, laser, electroporation, high-frequency ultrasound or other thermal modalities) to prevent wavelets or electrical signals/impulses that propagate through the atrial tissue to sustain atrial fibrillation or produce atrial flutter, atrial tachycardia, or another arrhythmia.

Many conventional approaches in applying energy to the atrial tissue face difficulties in attempting to create a complete lesion pattern that prevents propagation of the electrical impulse across the lesion pattern. Some factors attributable to these difficulties are tissue contact throughout the length of the electrode(s) is/are not consistent causing variability in the transmission of energy throughout the target length of ablated/coagulated tissue. Moreover, surrounding anatomic features also contributes to the difficulty in creating a complete lesion pattern. As a result, an incomplete lesion or lesion pattern includes one or more gaps of viable or semi-viable tissue that allows propagation of wavelets through tissue and through the lesion pattern.

Another problem with ablation treatment is ensuring creation of a complete curvilinear, transmural lesions is the presence of convective cooling on the opposite surface of the atrium Traditionally, atrial coagulation patterns were only completed using endocardial coagulation lesions. In such procedures, the physician introduced one or more intravenous catheters through the vasculature to atrial tissue. Endocardial coagulation suffers a drawback in that the physician cannot easily visualize the site being ablated. Furthermore, endocardial coagulation carries a risk of complications due to ablating outward from the endocardial surface including esophageal fistula, thromboembolic complications from coagulum formation, PV stenosis, phrenic nerve palsy and lung damage. Aside from the risks, it is difficult to create complete linear lesion lines via an endocardial approach.

Recently, systems have been developed to ablate the cardiac tissue on the epicardium and endocardium. Epicardial coagulation allows for more comprehensive bi-atrial lesion patterns at the expense of procedural complexity and time. However, many current procedures require significant manipulation of other tissue structures to create the desired lesion pattern. For example, many procedures require one or more ports or trocars placed in a chest wall and/or deflation of a lung to access the target site.

The improved methods and devices described herein offer an improvement to reach areas of tissue via improved steering of devices. Additional improvements involve identifying the devices using virtualization software.

The improved methods and devices described herein offer improved access to tissue regions within the body, especially those organs in the thoracic cavity. Variations of these methods and devices described herein improve on the ability to treat atrial fibrillation and ventricular tachycardia ablation and can treat selected tissue regions in a precise manner.

SUMMARY OF THE INVENTION

Variations of the systems, devices and methods described herein provide for improved percutaneous endoscopic ablation procedures by allowing improved access to cardiac tissues within the pericardial sac. Additional variations of devices, systems and methods described herein can be used in areas outside of the cardiac space. Variations of the methods, systems and devices described herein include combinations of features of the various embodiments or combination of the embodiments themselves wherever possible.

The present disclosure includes steerable medical ablation devices. For example, one variation of a device includes an ablation assembly; a shaft having a distal end and a proximal end, the ablation assembly located at the distal end, the shaft having a distal section adjacent to the distal end and a flexible section being proximally spaced from the distal section; a handle located at the proximal end, the handle having an actuator; a steering member coupled between the actuator and the distal section of the shaft, such that movement of the actuator controls a deflection of the distal section, where the deflection of the distal section is limited to a first plane; and where the proximal section of the shaft is flexible and limited to bend in a second plane, where the second plane is perpendicular to the first plane.

The medical device can further include a proximal section between the proximal end and the flexible section, where a flexibility of the proximal section is less than a flexibility of the flexible section. Variations of the device can include wherein an ablative element of the ablation assembly that is exposed at an opening, where the opening is parallel to the first plane.

The medical devices described herein can further include further comprising a plurality of navigation elements located about an exterior of the housing, where at least a first navigation element in the plurality of navigation elements is configured to provide a first virtual image in an electroanatomic mapping system, and where at least a second navigation element in the plurality of navigation elements is configured to provide a second virtual image in the electroanatomic mapping system, where the first virtual image represents the medical device and where the second virtual image represents an orientation of the ablation assembly relative to the medical device. Variations of such devices can include an ablation element that is a helical electrode. Deflection of the housing can be controlled using the actuator in some variations of the device.

Another variation of the device includes a medical device for accessing a region of tissue to serve as an access device for one or more separate medical devices. For example, such an access device can include a shaft having a distal end and a proximal end with a passage extending there-through, the shaft having a distal section adjacent to the distal end and a flexible section being proximally spaced from the distal section; a handle located at the proximal end, the handle having an actuator; a steering member coupled between the actuator and the distal section of the shaft, such that movement of the actuator controls a deflection of the distal section, where the deflection of the distal section is limited to a first plane; and where the proximal section of the shaft being flexible and limited to bend in a second plane, where the second plane is perpendicular to the first plane.

The devices described herein can further include a locking mechanism on the handle, where the locking mechanism secures the distal section of the shaft in an arcuate shape.

Variations of the devices can include shafts that comprises a plurality of lumens, where at least one lumen comprises a flushing port, where the flushing port is fluidly coupled to a valve at the handle. Additional variations can include shafts that comprise one or more guidewire lumens extending through the shaft (and ablation assembly if present).

Variations of the shafts can include one or more slotted tubes, wherein a first portion of the slotted tube aligns with the distal portion of the shaft and a second portion of the slotted tube aligns with the flexible section, where the first portion of the slotted tube comprises a plurality of first slots and the second portion of the slotted tube comprises a plurality of second slots, where the first and second slots are situated 90 degrees apart on the slotted tube.

Variations of the access devices can further include one or more dilators that extend through the shaft, the dilator having an atraumatic tip extending through the distal end of the shaft, the dilator further including a hub that is configured to removably lock with the handle.

The present disclosure also includes devices that are adapted for use in an electroanatomic mapping system. For example, one such device includes a treatment device adapted to be coupled to a vacuum source and for coagulating soft tissue, where the surgical device can include an elongate member comprising a side wall and a lumen, where the lumen is fluidly coupleable to the vacuum source; a tissue heating element adjacent the side wall within the elongate member; and an opening through the side wall in communication with the lumen and exposing the tissue heating element where the tissue heating element is positioned within the opening such that when placed against tissue, the tissue heating element coagulates soft tissue at the opening; and at least a first navigation element located on the elongate member, where the first navigation element is configured to produce a first virtual image that represents at least a portion of the elongate member in the electroanatomic mapping system, at least a second navigation element configured to produce a second virtual image that represents an orientation of the opening in the sidewall exposing the element relative to the housing.

A variation of the surgical device can include a side wall that is flexible to conform to soft tissue to form a seal against the tissue upon application of a vacuum from the vacuum source so that the vacuum pulls tissue within the opening causing the tissue to contact the tissue heating element. such that the tissue heating element is offset from the opening.

Examples of coagulation devices that can be used with the devices described herein include for creating lesions are disclosed in commonly assigned patents: U.S. Pat. No. 6,893,442 filed on Jun. 14, 2002, issued on May 17, 2005; U.S. Pat. No. 7,410,487 filed on Mar. 30, 2005, issued on Aug. 12, 2008; U.S. Pat. No. 9,603,657 filed on Jun. 6, 2008, issued on Mar. 28, 2017; U.S. Pat. No. 7,063,698 filed on Apr. 29, 2003, issued on Jun. 20, 2006; U.S. Pat. No. 7,780,661 filed on May 12, 2006, issued on Aug. 24, 2010; U.S. Pat. No. 7,758,578 filed on May 12, 2006, issued on Jul. 20, 2010; U.S. Pat. No. 7,803,155 filed on May 23, 2006, issued on Sep. 28, 2010; U.S. Pat. No. 9,603,658 filed on Jun. 22, 2010, issued on Mar. 28, 2017; U.S. Pat. No. 8,858,552 filed on Aug. 6, 2010, issued on Oct. 14, 2014; U.S. Pat. No. 7,572,257 filed on Aug. 18, 2005, issued on Aug. 11, 2009; U.S. Pat. No. 8,034,053 filed on Jun. 16, 2009, issued on Oct. 11, 2011; U.S. Pat. No. 5,320,065 filed on Apr. 21, 2006, issued on Jul. 19, 2013; U.S. Pat. No. 8,998,900 filed on Apr. 21, 2006, issued on Apr. 7, 2015; U.S. Pat. No. 5,054,116 filed on Nov. 9, 2006, issued on Aug. 3, 2012; U.S. Pat. No. 9,439,714 filed on Nov. 9, 2006, issued on Sep. 13, 2016; U.S. Pat. No. 9,808,280 filed on Apr. 19, 2007, issued on Nov. 7, 2017; U.S. Pat. No. 8,235,990 filed on Apr. 19, 2007, issued on Aug. 7, 2012; U.S. Pat. No. 8,454,598 filed on Feb. 3, 2012, issued on Jun. 4, 2013; and U.S. Pat. No. 9,308,042 filed on May 30, 2013, issued on Apr. 12, 2016. Examples of coagulation devices that can be used with the devices described herein are also found in US Publications: US20170042612 filed on Oct. 26, 2016, published on Feb. 16, 2017; US20150250538 filed on May 8, 2015, published on Sep. 10, 2015; US20120179150 filed on Oct. 10, 2011, published on Jul. 12, 2012; US20150265338 filed on Feb. 27, 2015, published on Sep. 24, 2015; US20080114355 filed on Nov. 9, 2006, published on May 15, 2008; US20170215942 filed on Sep. 8, 2016, published on Aug. 3, 2017; US20180028225 filed on Oct. 5, 2017, published on Feb. 1, 2018; and US20160220306 filed on Apr. 8, 2016, published on Aug. 4, 2016. The entirety of each of which is incorporated by reference herein.

BRIEF DESCRIPTION OF DRAWINGS

FIGS. 5B to 5D illustrate an example of the features of a steering actuator with the handle assembly removed for purposes of illustration.

DETAILED DESCRIPTION

Methods and devices are disclosed herein for providing accesses to tissue and/or treating tissue. The devices and methods are suitable for minimally invasive surgery or open surgical procedures. The methods and devices described herein discuss the treatment of cardiac tissue for purposes of illustration. However, the methods and devices can be applied in any application where tissue is treated (e.g., via such modes including heating, cooling, mechanical).

The devices described herein allow for creation of cardiac lesion patterns on cardiac surfaces. However, the methods and techniques are applicable to non-cardiac treatments as well. Variations of the devices, methods and procedures described herein include combinations of features of the various embodiments or combination of the embodiments themselves wherever possible.

Figure 1:
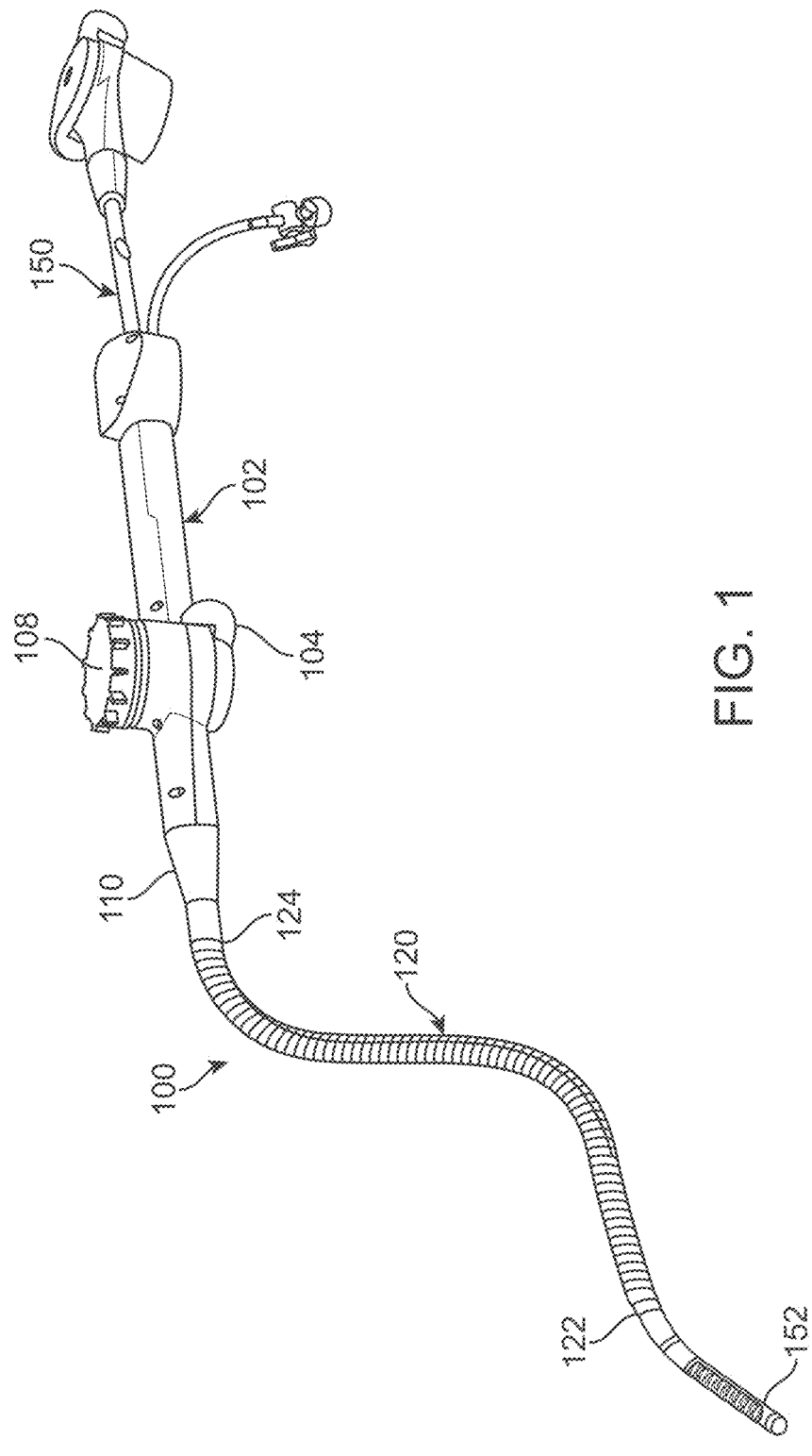
FIG. 1 illustrates a variation of a medical system for accessing a region of tissue.

FIG. 1 illustrates a variation of a medical system 100 for accessing a region of tissue. In the illustrated variation, the medical system 100 serves as an access device for a secondary device 150, such as an ablation device or other medical treatment/imaging/sensing device. Alternatively, as discussed below, the medical system 100 can include one or more working components on a distal end of the device 100, such that the medical system 100 itself performs medical treatment/imaging/sensing.

The variation of the system 100 illustrated in FIG. 1 includes a handle 102 having an actuator 104. As discussed in detail below, the actuator 104 allows for directional steering of a distal end 122 of the shaft 120. Although not illustrated, the actuator 104 can employ any number of steering mechanisms or members that can direct or articulate the distal end 122 of the shaft 120 in a desired direction. Such mechanisms can include, but are not limited to, one or more steering wires, tubular members, etc. The handle 102 of the system 100 can also include a locking mechanism 108 that maintains the distal end 122 in a desired position (or maintains a distal portion of the shaft 120 that is adjacent to the distal end 122) in a desired arcuate profile.

Figure 2A:
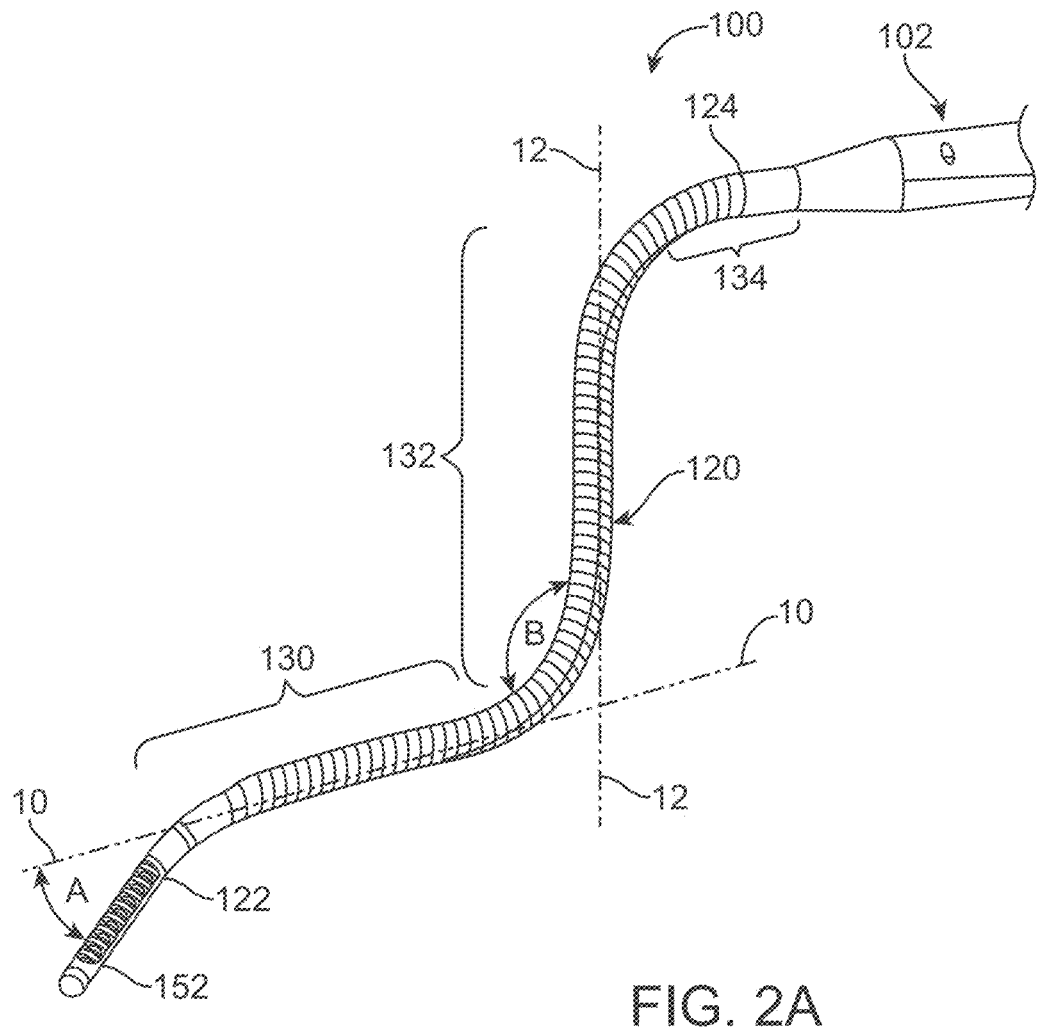
FIG. 2A illustrates a variation of a shaft of a system as disclosed herein.

FIG. 2A illustrates a variation of a shaft 120 of a system 100 as disclosed herein. In this variation, the shaft comprises a distal portion 130 that is adjacent to the distal end 122 of the shaft 122. As noted herein, the distal portion 130 of the shaft 122 is coupled to the actuator (not shown in FIG. 2A) of the system handle 102, which controls movement or steering of the distal end 122 and/or distal portion 130. The shaft 122 also includes a flexible section 132 that is proximally spaced from the distal portion 130. The flexible section 132 allows a user to manipulate the system 100 using the handle 102, where such manipulation ultimately directs the distal end 122 of the shaft. For example, in the illustrated example shown in FIG. 2A, the distal portion 130 of the shaft 120 is configured for bi-directional movement in a plane that contains line 10. This bi-directional movement allows for the distal end 122 to move through angle A within the plane defined by line 10. The flexible section 132 of the shaft 120 is configured to flex within a plane containing line

12. Accordingly, flexible section 132 can bend as shown by angle B to assume the profile shown in FIG. 2A. In this variation, line 10 is perpendicular to line 12, which means that the actuator (not shown) can manipulate a deflection of the distal section 130, where the deflection of the distal section is limited to a first plane containing line 10, while the flexible section 132 of the shaft is limited to bend in a second plane containing line 12, where the second plane is perpendicular to the first plane. Alternate variations of the system 100 allow for the first plane and second plane to be non-orthogonal.

One benefit of the configuration shown in FIG. 2A is that the distal end 122 of the system 100 can be applied to tissue surfaces without the need for adjacent tissue structures to provide an opposing force. For example, when a cardiac device is advanced within the pericardium to an atrial surface, a device with the configuration described herein can engage the atrial surfaces without needing support from the adjacent pericardial sac. The operator can navigate the distal end and distal portion of the device to a desired region of tissue and apply torque or downward force on the distal end 122 using the handle 102 of the device. FIG. 2A also illustrates the shaft 120 as having a third or proximal region 134 that is less flexible than the middle or flexible region 132.

Figure 2B:
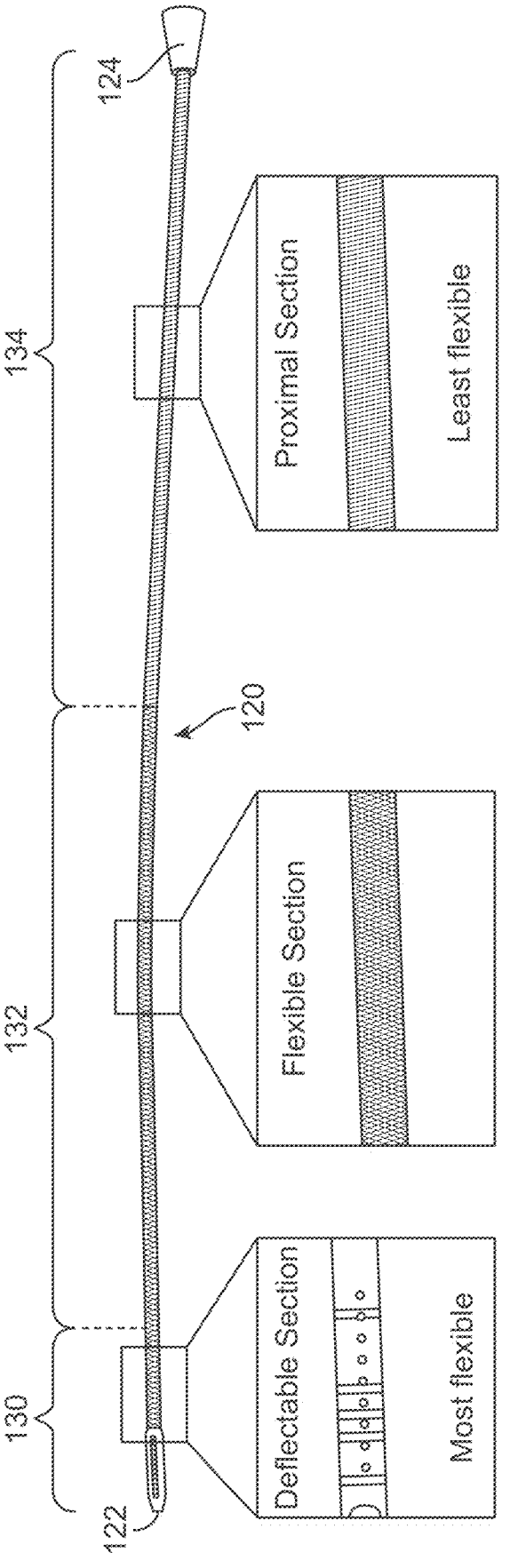
FIG. 2B illustrates another variation of a shaft having a construction as discussed herein where the shaft has properties and a construction that varies along its length.

FIG. 2B illustrates another variation of a shaft 120 having a construction as discussed herein where the shaft 120 has properties and a construction that varies along its length. For instance, the bending stiffness of the shaft 120 can vary or decrease in a proximal to distal direction. Such a configuration provides a proximal section 134 that is the least flexible, a middle or flexible section 132 that is more flexible than the proximal section, and a deflectable distal portion 130 that is the most flexible but only in a direction or plane that is different than the planes in which the other portions of the shaft can flex.

Figure 3A:
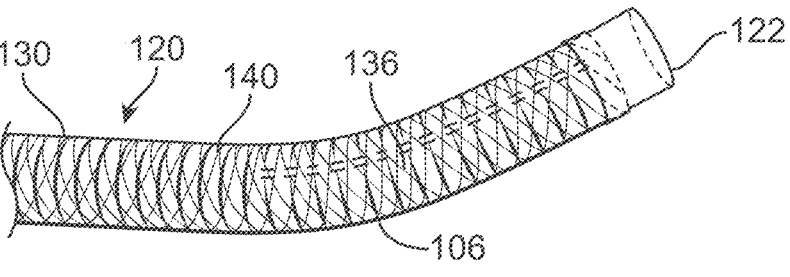
FIGS. 3A and 3B illustrate examples of a distal portion of a shaft for purposes of demonstrating an inner construction of the shaft with bidirectional steering of the distal portion in a single plane.

FIG. 3A illustrates an example of a distal portion 130 of a shaft 120 for purposes of demonstrating one example of an inner construction of the shaft 120 with bidirectional steering of the distal portion 130 in a single plane. In this variation, the shaft 120 is constructed from a transparent polymer to better show components forming the shaft 120. Clearly, other polymers are within the scope of this disclosure. In those variations where the shaft 120 is part of an access device, the distal end 122 of the distal portion 130 can include a soft tip construction. It is also understood that the soft tip may consist of multiple changes to these or other components to blend properties from the proximal and distal sections.

As shown, the shaft 120 comprises a slotted tube 140 construction within the polymer and a braid or wrapped wire 136 (e.g., a stainless steel braid) located about the slotted tube 140. Other constructions used for catheter technology can be incorporate within the scope of the sheaths under the present disclosure.

Figure 3B:
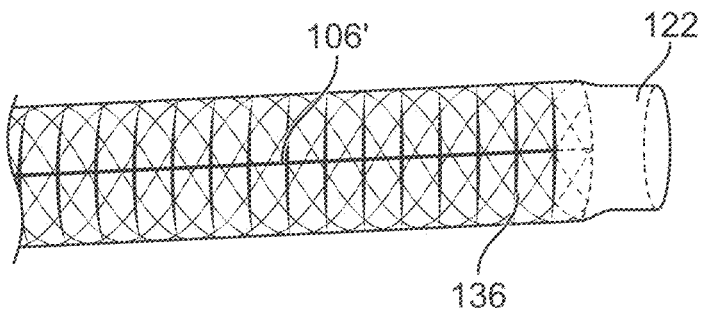

FIGS. 3A and 3B also show a variation of a steering member 106 that coupled near the distal tip 122 of the shaft 120. The steering member 106 can be coupled between the actuator (not shown in FIG. 3A) and the distal portion 130. While any number of steering members 106 can be used, the present variation uses two steering members 106 positioned on either side of the shaft 120. The steering members 106 can function as pull/push wires that are affixed to one or more portions of the tube 140.

Figure 3C:
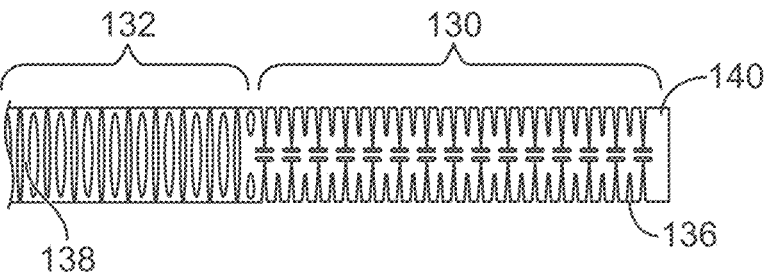
FIGS. 3C and 3D illustrate an example of a slotted tube that provides different bending characteristics required for different sections of the shaft.
Figure 3D:
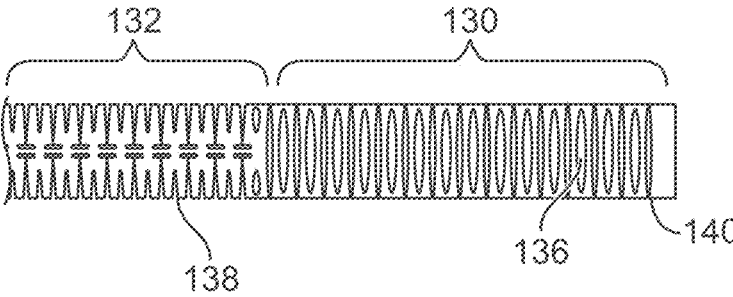

FIG. 3C illustrates a partial top view of the slotted tube 140 of FIGS. 3A and 3B. As shown, the slotted tube 140 can include multiple regions having different configurations, where each region corresponds to a region on the shaft as discussed above. For example, the distal region 130 of the shaft corresponds to a region in the slotted tube 140 that has a series of cutouts 136 that allow for bi-directional steering of the distal portion 130 in the plane as discussed above. As shown, the flexible portion 132 of the shaft corresponds to a region in the tube 140 where a plurality of cutouts 138 are oriented in a manner (e.g., rotated 90 degrees as compared to cutouts 136) to permit flexure of the flexible region 132 in a different plane than the first plane in which the distal section can be steered. FIG. 3D illustrates a side view of the slotted tube 140 for better illustration of the rotated cutouts 136 and 138 in the corresponding distal section 130 and middle (or flexible) section 132.

As noted herein, construction of the shaft can include extruded silicone with one or more lumens to accommodate use of vacuum, perfusion, guidewires, and electrical connections through the shaft. The variation in mechanical properties and construction of the shaft may be achieved by changing the variations of the shaft jacket and the shaft jacket can be compromised of multiple materials in multiple configurations. For instance, the shaft jacket of the proximal shaft section can comprise a PET liner covered in a stainless-steel braid and an outer polyolefin jacket. The flexible shaft section can include a stainless-steel braid and an outer polyolefin jacket. The deflectable distal section can comprise silicone alone, without polyolefin, braiding, or PET liners. Again, the construction of the device can vary and the examples discussed are meant to show one possible construction of the shaft.

Figure 4A:
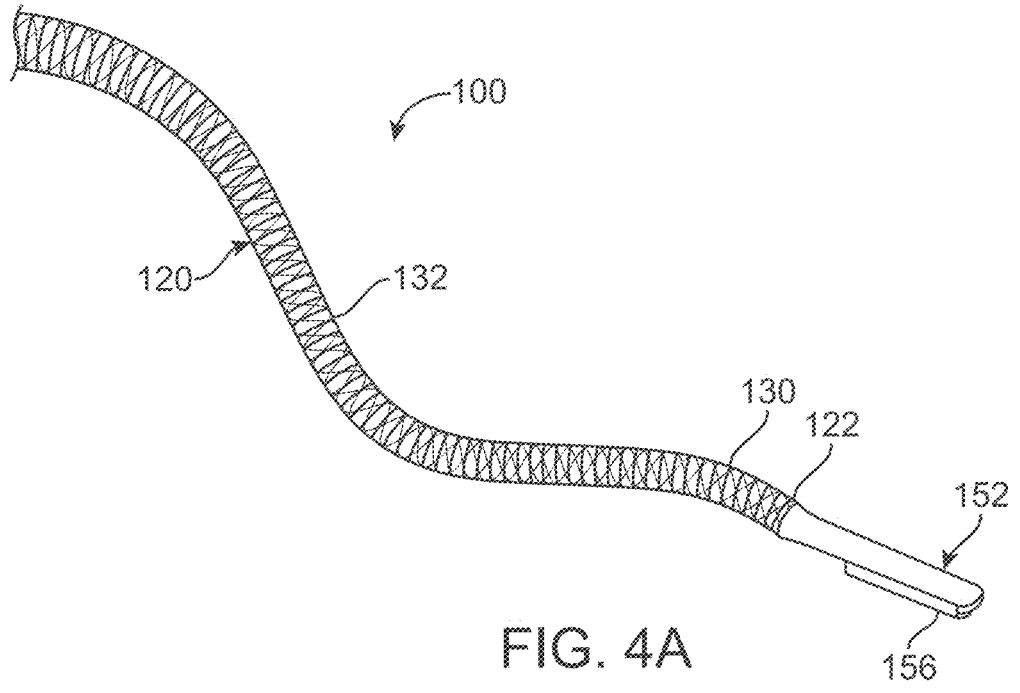
FIG. 4A illustrates another variation of a medical system having a shaft as described herein with a working portion (e.g., an ablation assembly) located at the distal end of the shaft.

FIG. 4A illustrates another variation of a medical system 100 having a shaft 120 as noted above. However, the variation illustrated in FIG. 4A includes a working portion 152 located at the distal end 122 of the shaft 120. In this variation, the working portion 152 comprises an ablation housing similar to those described in the above reference commonly assigned patent applications. As illustrated, a working surface 156 of ablation component 152 is exposed in an orthogonal direction to the plane of movement of the distal portion 130 of the shaft 120.

Figure 4B:
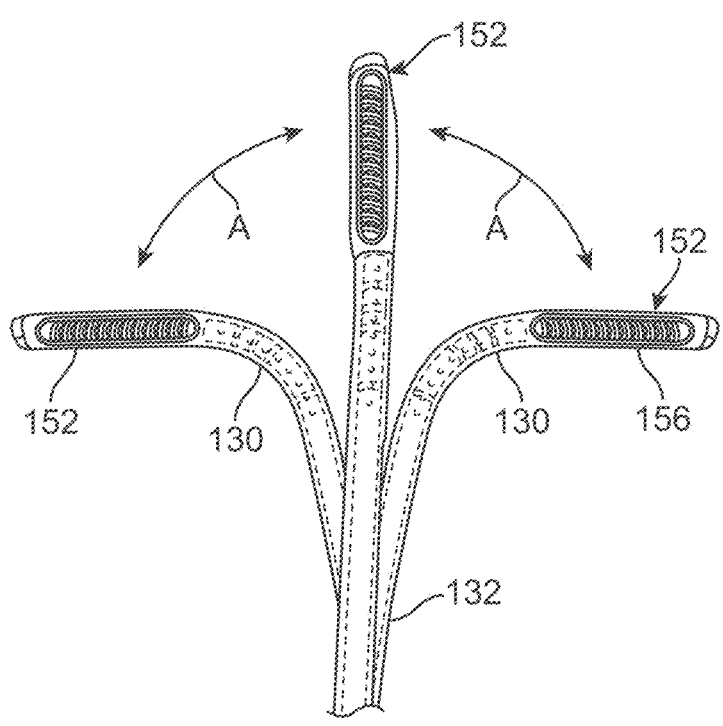
FIG. 4B illustrates the working portion and distal portion of the shaft with bi-directional steering in a single plane.

FIG. 4B illustrates a partial bottom view of the device of FIG. 4B. As shown, the distal portion 130 of the shaft is configured for bi-directional movement through angles A in a plane as discussed above. This permits positioning of the working surface 156 and energy transfer element contained therein.

Figure 4C:
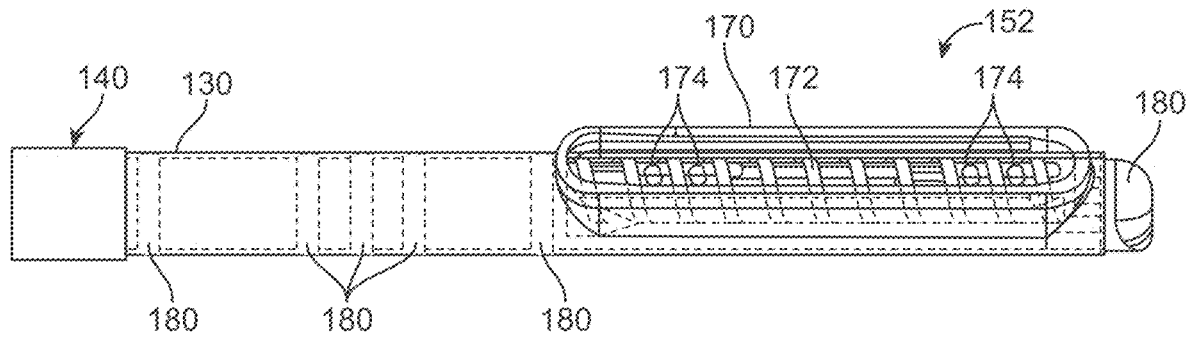
FIGS. 4C to 4E illustrates variations of an ablation component of an ablation device described herein.

FIG. 4C illustrates a variation of an ablation component 152 of the device of FIGS. 4A and 4B. Again, the features of the device can include a steerable ablation catheter/device with a suction pod 170, an ablation electrode or coil 172, electrodes 174 for pacing or sensing cardiac tissue, and navigation electrodes 180

The distal tip section 152 can be flexible in all axes perpendicular to the length of the shaft 120 and may include bidirectional steering controlled by the handle (not shown in FIG. 4C. The ablation electrode 172 can be helical in shape; however, other shapes can be used to engage the tissue. The ablation electrode 172 may be made of platinum-iridium, stainless steel, copper, silver, gold, and other materials known in the art.

Figure 4D:
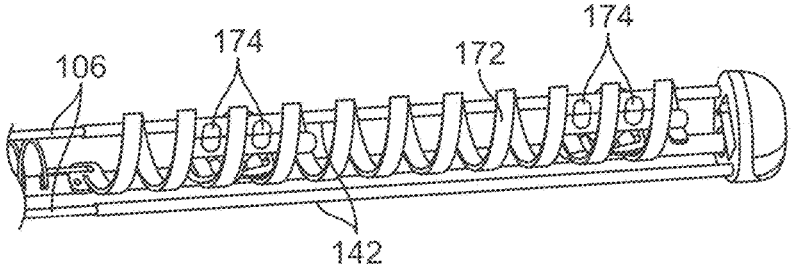

FIG. 4D illustrates one example of a steering configuration in a sub-assembly of the ablation component 152. As shown, steering members 106 (such as pull wires or cables) can extend through hypotubes 142 that are connected to a bullet nose 144, which maintains the helical ablation coil 172 in an undeformed shape during deflection. The bullet nose 144 can also serve as an electrode and an atraumatic tip.

Figure 4E:
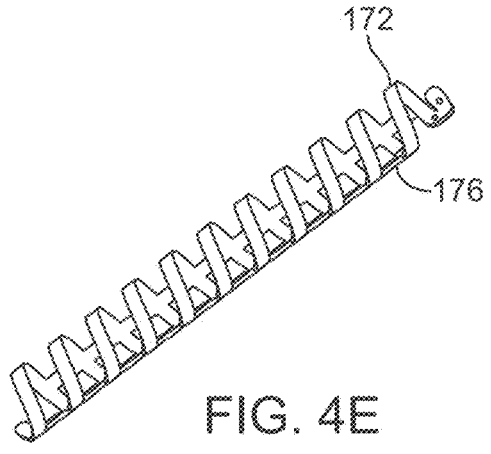

FIG. 4E illustrates an alternative variation for a helical ablation element 172, where the element 172 includes a spline 176 that minimizes coil deformation during deflection of the element 172.

Figure 5A:
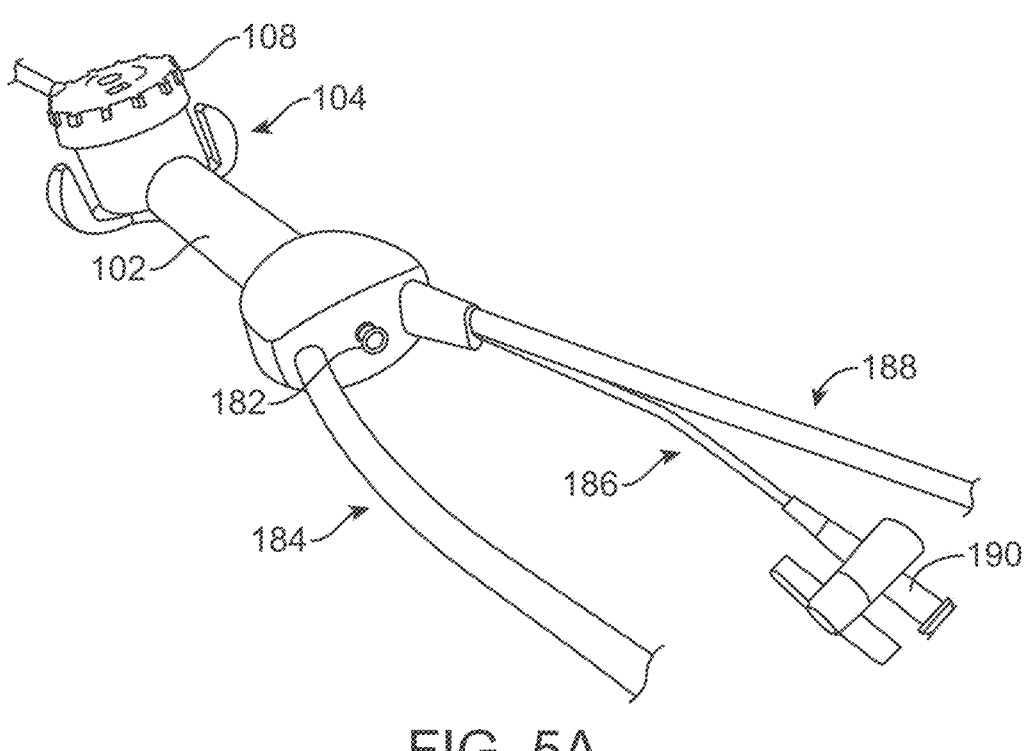
FIG. 5A illustrates a rear view of a handle for use with an ablation device.

FIG. 5A illustrates a rear view of a handle 102 for use with the ablation device shown in FIG. 4A. As shown, the handle 102 can include a steering actuator 104 that deflects the distal portion and/or the ablation element (neither shown in FIG. 5A). The handle 102 can include a steering lock 108 that sets the steering actuator (and thus the distal end of the device) in a desired deflected position when the steering actuator 194 is released or returns to the straight configuration. The handle 102 can also include one or more lumens 182 for a guidewire, perfusion line 186 (with or without a hemostasis valve 190 to interface with the steerable ablation catheter/device) that provides saline or other fluids for thermal regulation during ablation, a vacuum line 188 to apply suction through the distal end of the device, a guidewire lumen for tracking the device over, and electrode wiring 184. Electrode wiring may separate the high power (ablation) wiring from wiring for the pace/sense electrodes or the navigation electrodes in any configuration.

The handle 102 can comprise any number of configurations. In the illustrated example, the handle consists of joined halves with a steering mechanism 104 capable of actuating the distal end of the shaft in a bi-directional manner.

Figure 5D:
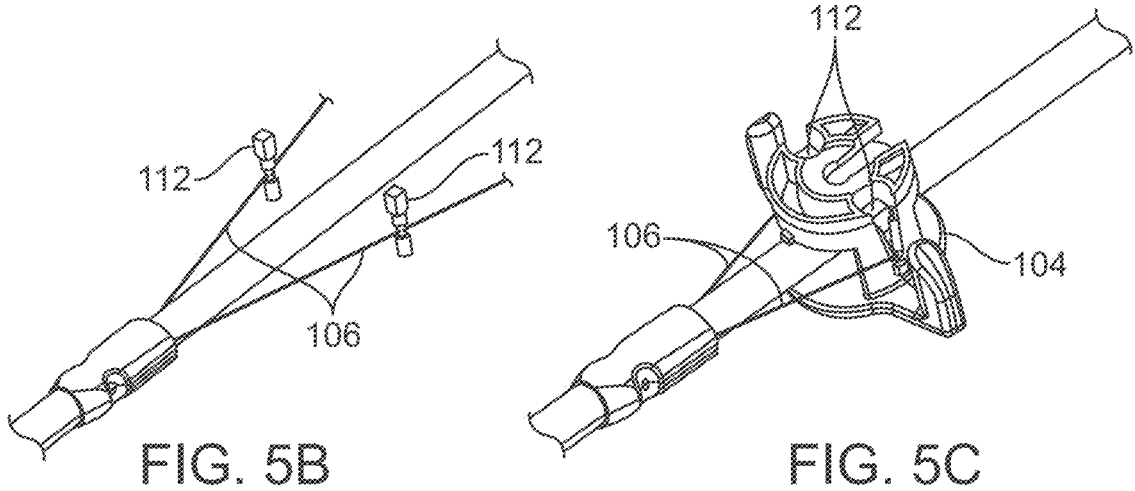
Figure 5D:
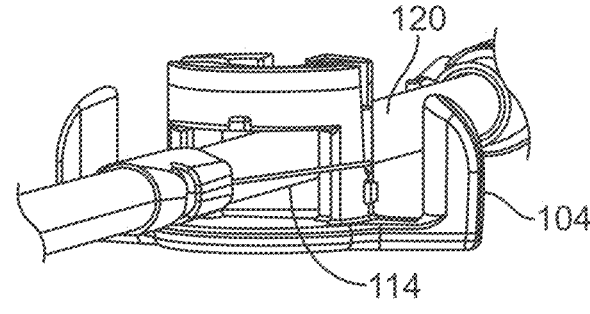

FIGS. 5B to 5C illustrate an example of the features of a steering actuator 104 with the handle assembly removed for purposes of illustration. The steering actuator 104 can serve multiple functions such as setting the tension in the pull-wires and actuating (rotating) while maintaining an open orifice for the shaft to run through. One method of setting the tension in the pull-wires 106 is to affix fasteners 112, such as banjo screws to the pull-wires 106 and then to use rotation of the fasteners with respect to the steering actuator as a means to reliably set the pull-wire tension. In this method, the banjo screws are advanced over the pull-wires (exposed at a strain relief) from the proximal direction until they are proximal, but in close proximity to the steering actuator. Then, the fasteners then affixed via solder or other means known in the art to the pull-wires 106. The affixed fasteners can then be set into the steering actuator 104 (as shown in FIG. 5C) and rotated until the correct amount of tension is applied and then pressed into the steering actuator, setting the tension and locking the position of the fasteners relative to the steering actuator. The fasteners can incorporate multiple rotations to set the tension on the pull wires. FIG. 5D illustrates an offset view of the steering actuator 105 illustrating an opening 114 that allows for rotation of the steering actuator 104 without impinging on the shaft 120.

Figures 6A, 6B, 6C, 6D:
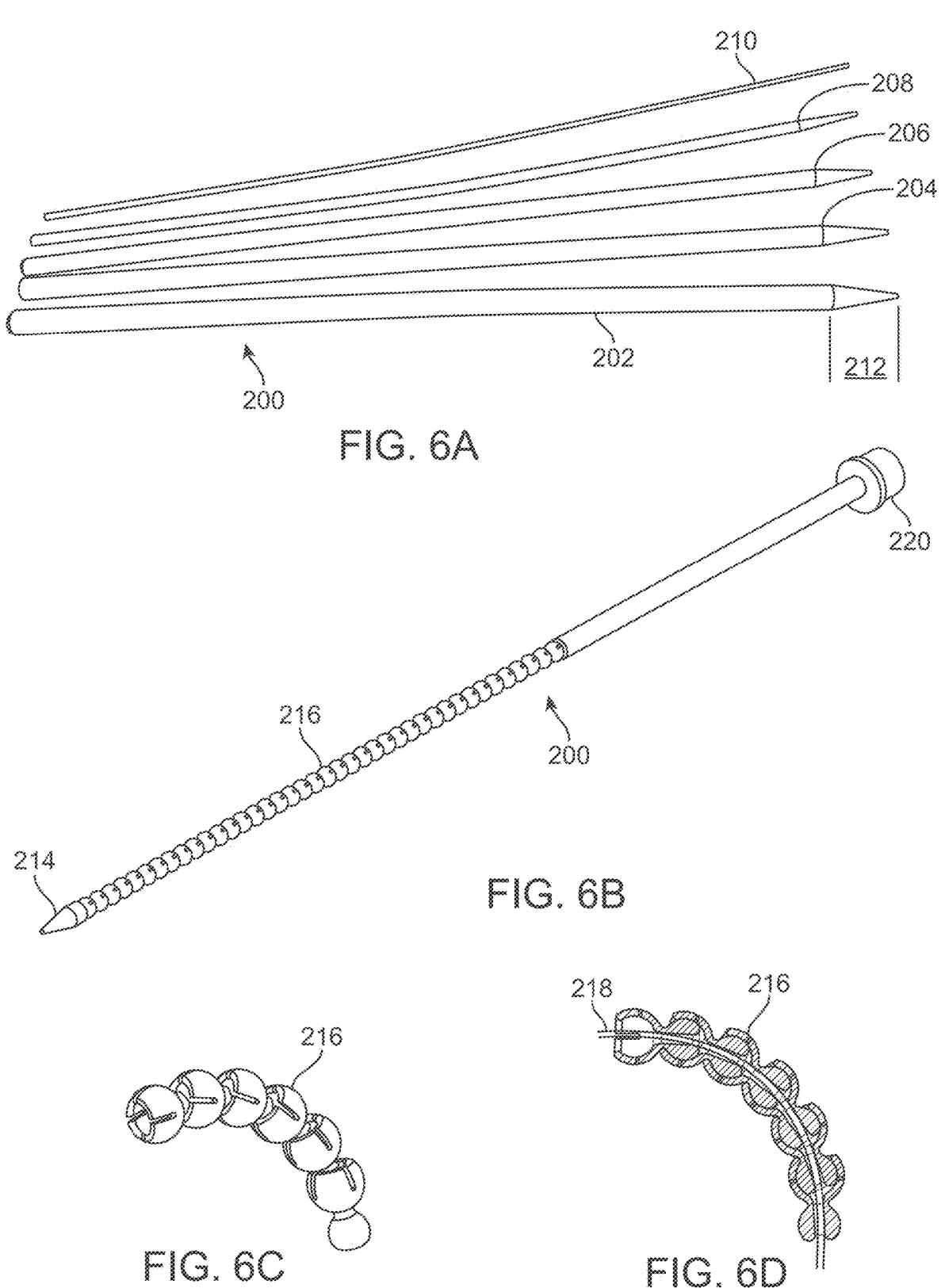
FIGS. 6A to 6F illustrate various dilator components for use with an access device of the present disclosure.

FIG. 6A illustrates a dilator component 200 that can be included as a part of the steerable sheath system when used as an access device as shown in FIG. 1. The sheath dilator 200 typically is a removable piece of the steerable sheath that fits inside a passage of the shaft and has a guidewire lumen allowing for tracking over a guidewire or similar structure.

FIG. 6A illustrates one variation of a dilator set 200 comprising a series of dilators 202 to 210 of varying sizes. In each case, the dilators 202 to 210 can include a uniform taper length 212 that allows for consistent dilation or dissection of tissues regardless of the diameter of the dilator.

Typically, the dilators 200 for use with the systems described herein include a guidewire lumen along a central axis, a tapered/atraumatic nosecone, a flexible shaft section, and a locking feature on the proximal end. FIG. 6B illustrates a variation of an additional dilator 200 having an atraumatic tip with a locking hub 220 at a proximal end. Variations of the device allow for the locking hub to removably lock with the handle of the system. The locking feature engages with the proximal end of the steerable sheath handle in such a way that the nosecone of the steerable dilator extends from the distal end of the steerable sheath. In typical use, the steerable dilator is inserted into the steerable sheath and locked prior to use. Then, a guidewire is fed through steerable dilator in the distal-to-proximal direction. The steerable sheath system (sheath and dilator) are then advanced over the wire into the body, with the nosecone serving as an atraumatic feature during advancement.

FIG. 6C illustrates a plurality of components 216 of the dilator of FIG. 6B, which permits flexing or articulation of the dilator. The components 216 form a flexible section, where each component 216 snaps together with an adjacent component, as in the ball and socket configuration shown. The internal geometry of these repeating segments is designed to track over a guidewire when the sheath is in a bent configuration. FIG. 6D illustrates a cross sectional view of the components of FIG. 6C, which illustrates a guidewire passage 218 that remains unobstructed through flexing of the dilator. Should we say that off the shelf dilators may also be used?

Figures 6E, 6F:
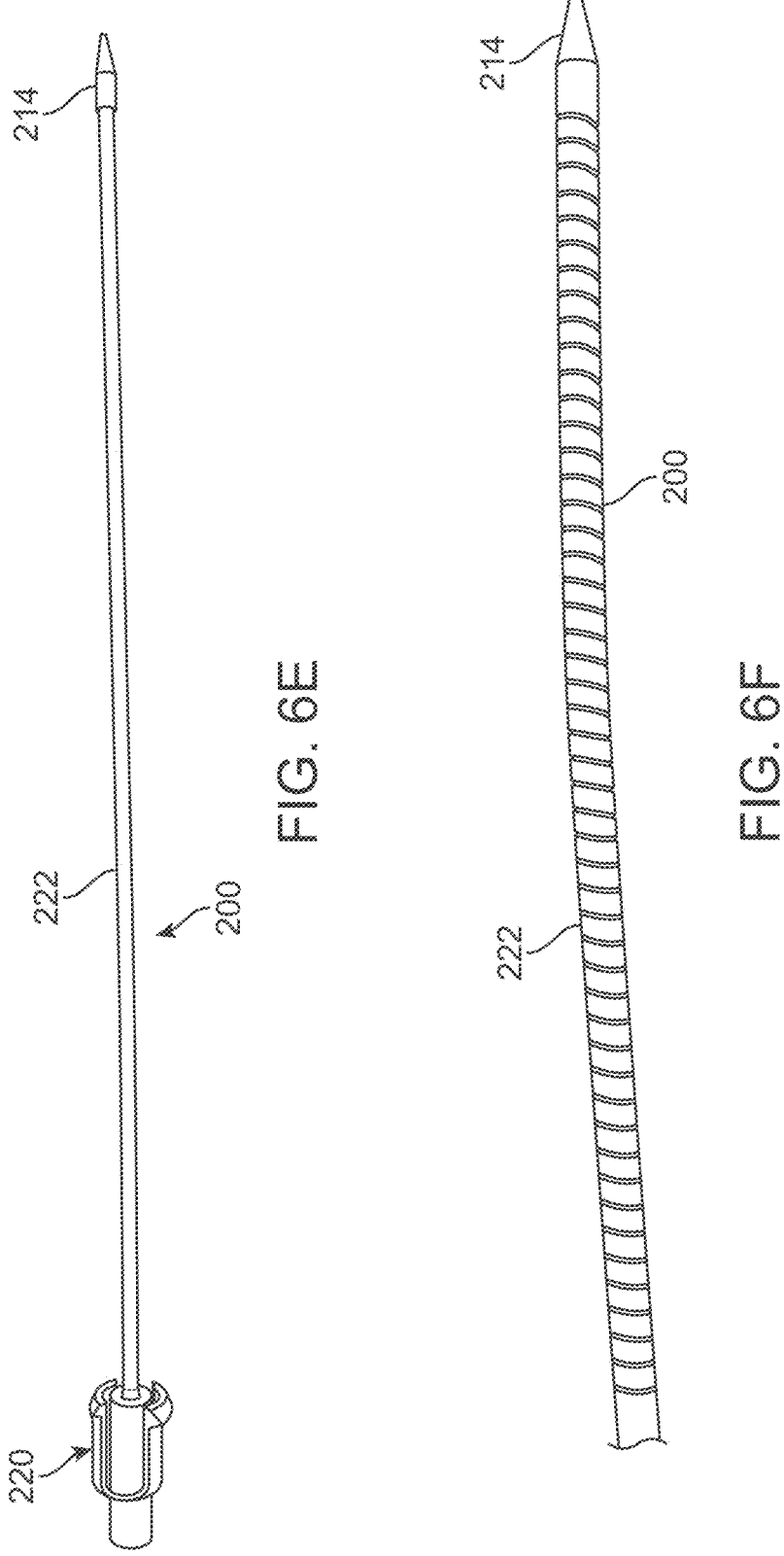

FIGS. 6E and 6F illustrate additional dilator 200 components for use with the system. FIG. 6E illustrates a dilator 200 having a guidewire lumen (not shown), an atraumatic nosecone 214, a flexible shaft 222, and a proximal locking hub 220 to attach to the proximal end of the handle. FIG. 6F illustrates a similar dilator with a spiral cut shaft 222. Two embodiments are shown: the top embodiment has a flexible coil.

As discussed above, the devices of the present disclosure can include navigation electrodes (180 in FIG. 4C), which allow for remote detection of the orientation of the associated device with an electroanatomic mapping system (such as the CARTO mapping system from Biosense, Diamond Bar, CA, USA). In the illustrated examples, the navigation electrodes are shown affixed to an ablation device, however, the navigation electrodes can be used on any device described herein. For example, the navigation electrodes can be affixed to the shaft of the access device discussed above.

Figure 7A:
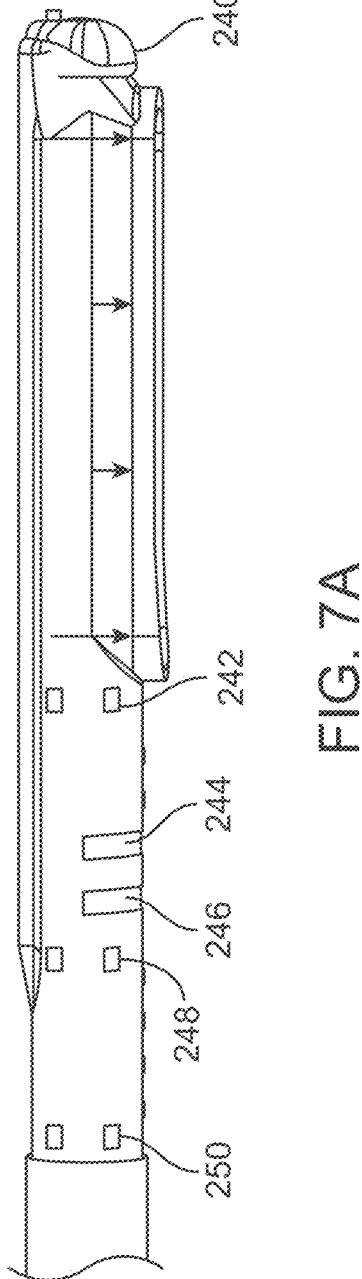
FIGS. 7A and 7B illustrate different configurations of ring electrode exposure where the ring electrode exposure affects how the electrode is observed as a navigation element in an electroanatomic mapping system.
Figure 7B:
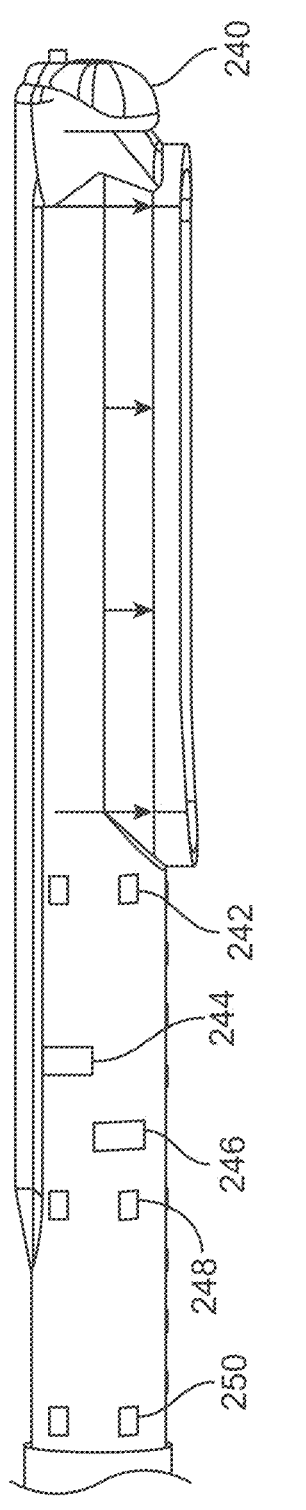

The navigation electrodes can encircle the ablation tip as shown in FIG. 4C. However, alternate variations can include electrodes that do not encircle the shaft or device. FIGS. 7A and 7B illustrate different configurations of ring electrode exposure. Position electrodes (240, 242, 244, 246, 248, and 250) can be circumferentially symmetrical so that the electrical "center" or "centroid" is at the geometric center of the ring. Orientation electrodes (244 and 246) can be circumferentially asymmetric, so that the electrical "center" or "centroid" does not match the geometric center of the ring. For instance, in configuration 1, rings 244 and 246 produce an electrical signal/location for the electrodes that are towards the direction of energy delivery. Conversely, in configuration 2, ring 244 would have an electrical signal/location for the electrode in the direction away from energy delivery while ring 246 has an electrical signal/location for the electrode in the direction of energy delivery.

Placement of the navigation electrodes in a specific configuration on a device enables the creation of "virtual device" within mapping software, so that the location of the device is known relative to the anatomy (or "virtual anatomy"). Voltage fields from the mapping software can triangulate the electrode position based on the sensed electrode signal. Combining multiple electrode signals can create a "virtual catheter" or "virtual device". Methods and devices described herein uses these techniques to not only sense position of a catheter but also the orientation of the device, so that the user is always aware of the direction of energy delivery from the device.

Figures 8A, 8B, 9:
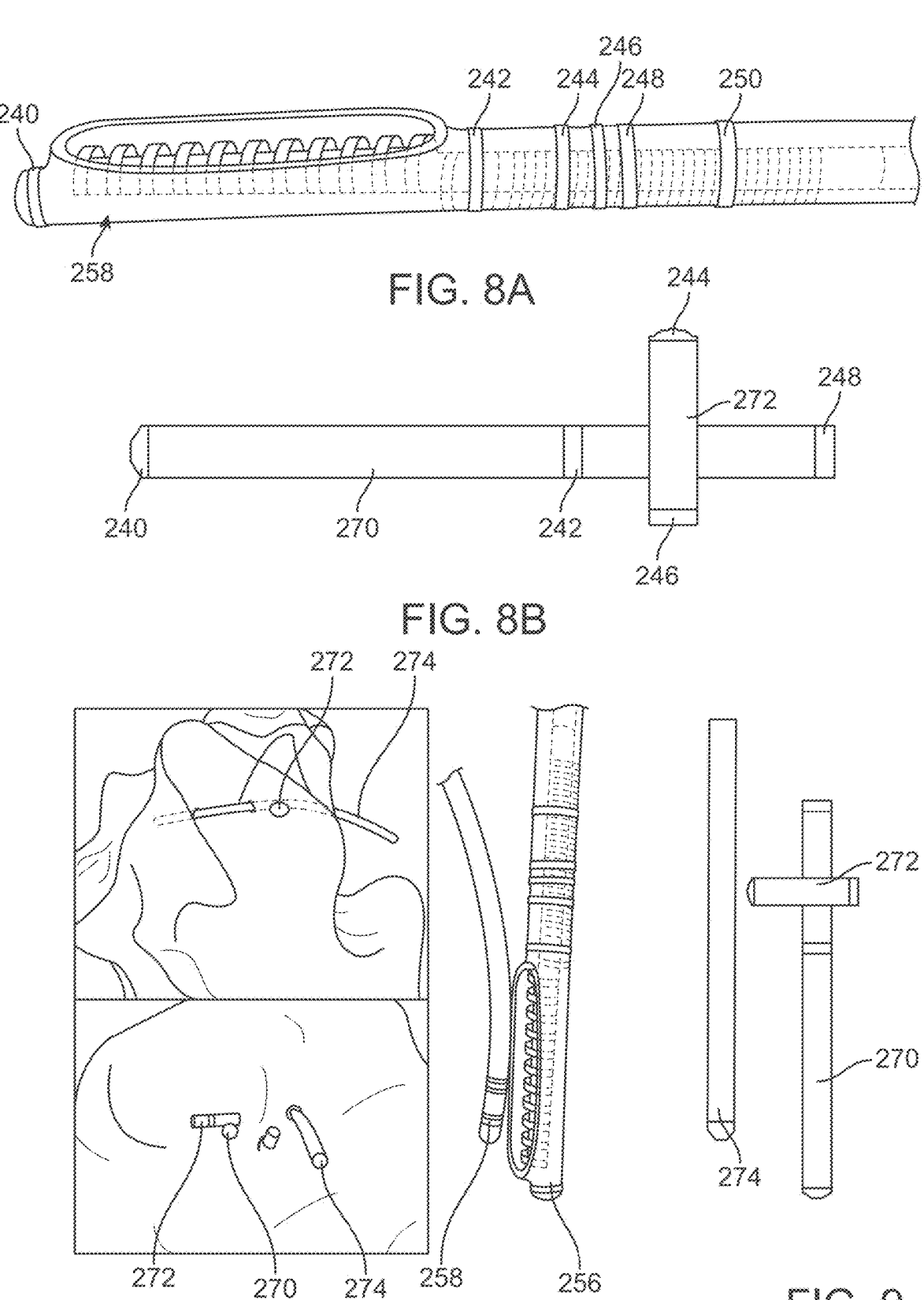
FIGS. 8A and 8B illustrate a variation of an ablation device, similar to that show in FIGS. 7A and 7B with navigation electrodes that are configured to show virtual position of the device as well as orientation of a treatment surface of the device (e.g., an electrode).
FIG. 9 illustrates a representation of the navigation electrodes used to determine position and orientation.

FIG. 8A illustrates a variation of an ablation device 258, similar to that show in FIGS. 7A and 7B with navigation electrodes that are configured to show virtual position of the device 258 as well as orientation of the electrode. In this variation, ring electrodes are placed on the device where electrodes 240, 242, 244, 246, 248, and 250 produce a "virtual catheter" as shown in FIG. 8B, with the electrodes 240, 242, 244, 246, 248, and 250 being virtually represented as shown. Electrodes 244 and 246 provide a virtual representation within mapping software that allows a user to identify a directional orientation of the electrode. bottom sketch). In this example, electrodes 240, 242, and 250 create the virtual catheter 270 shown in FIG. 8B. This virtual catheter 280 allows a user to determine device position using the mapping software. Navigation electrodes 244 and 246 produce a virtual indicator 272, which determines device orientation. This virtual orientation allows a user to identify the coil direction/direction of energy delivery from the coil/electrode. Note that the virtual catheters can be defined to be any size within the software, so it is typical to have the virtual indicator 272 appear to have electrodes off of the virtual catheter 270. This is desirable because it is easier to see the orientation of the virtual indicator 272. Electrode 248 from FIG. 8A is not used in this variation of virtual representation of FIG. 8B.

To create the virtual catheter 270, the electrode rings are fully exposed, for example that there is no silicone to insulate the ring electrode from the electric field. The position of the centroid of the ring electrode is determined by the software and represented as a virtual catheter. The end effect is that the virtual catheter 270 has accurate positioning that corresponds with the centerline of the three ring electrodes. This catheter could include a number of electrode configurations.

To create the virtual indicator 272, the electrode rings are partially exposed, meaning that silicone insulates a portion of the electrical signal. In the example above, ring three has been exposed on the coil side of the device (top of the image) and ring four has been exposed on the dorsal side of the device. The end effect is that the position of ring electrode four is biased towards the exposed, dorsal side of the device and electrode three is biased towards the exposed, coil side of the device, which produces the virtual indicator 272.

FIG. 9 illustrates a representation of the navigation electrodes used to determine position and orientation. In this setup, the device 256 was placed in a conductive tank and subjected to voltage fields. Then, the signals from the electrodes care read using a cardiac mapping software. A second, commercially available diagnostic catheter was then placed in the tank such that it was in close proximity to the coil/direction of energy delivery catheter 256.

The virtual catheters were visualized using the cardiac mapping software. The position of the ablation device 256 relative to the diagnostic catheter 258 is demonstrated by the virtual catheter 270 representing the ablation catheter 256 and virtual device 274 representing the diagnostic catheter 258. The orientation of the device and direction of energy delivery is verified by the virtual indicator 272, which has the distal virtual electrode pointing towards the commercial catheter.

In additional variations, additional electrode can be used to create additional virtual representations. For example, if an additional electrode (e.g. 248 in FIG. 8A) is used with electrode 246 to create another virtual indicator, then it would be possible to inform the user that energy was always applied in the open direction of the "v" formed by these two virtual indictors. Clearly, the orientation of the virtual catheter and/or virtual indicator can be adjusted through alternate electrode design on the device.

What is claimed is:

1. A medical device for accessing a region of tissue, the device comprising:

a shaft having a distal end and a proximal end with a passage extending there-through, the shaft having a distal section adjacent to the distal end and a flexible section being proximally spaced from the distal section;

a handle located at the proximal end, the handle having an actuator and a locking mechanism on the handle, wherein the actuator and locking mechanism are rotatable along the same axis;

a steering member coupled between the actuator and the distal section of the shaft, such that movement of the actuator controls a deflection of the distal section, where the deflection of the distal section is limited to a first plane, wherein the locking mechanism secures the distal section of the shaft in an arcuate shape by setting the actuator;

a dilator extending through the shaft, the dilator having an atraumatic tip extending through the distal end of the shaft, the dilator further including a locking hub that engages with a proximal end of the handle and is configured to removably lock with the handle; and wherein the proximal section of the shaft is flexible and limited to bend in a second plane, where the second plane is perpendicular to the first plane.

2. The medical device of claim 1, further comprising a proximal section between the proximal end and the flexible section, where a flexibility of the proximal section is less than a flexibility of the flexible section.

3. The medical device of claim 1, wherein the shaft comprises a plurality of lumens, where at least one lumen comprises a flushing port, where the flushing port is fluidly coupled to a valve at the handle.

4. The medical device of claim 1, further comprising a guidewire lumen extending through the shaft.

5. The medical device of claim 1, where the steering member comprises at least one pull wire affixed to the distal section of the shaft.

6. The medical device of claim 1, wherein the shaft includes a slotted tube configuration, wherein a first portion of the slotted tube aligns with the distal portion of the shaft and a second portion of the slotted tube aligns with the flexible section, where the first portion of the slotted tube comprises a plurality of first slots and the second portion of the slotted tube comprises a plurality of second slots, where the first and second slots are situated 90 degrees apart on the slotted tube.

7. A surgical device adapted to be coupled to a vacuum source and for coagulating soft tissue and for use with an electroanatomic mapping system, the surgical device comprising:

an elongate member comprising a side wall and a lumen, where the lumen is fluidly coupleable to the vacuum source;

a tissue heating element adjacent the side wall within the elongate member;

and an opening through the side wall in communication with the lumen and exposing the tissue heating element where the tissue heating element is positioned within the opening such that when placed against tissue, the tissue heating element coagulates soft tissue at the opening; and at least a first navigation element located on the elongate member, where the first navigation element is configured to produce a first virtual image that represents at least a portion of the elongate member in the electroanatomic mapping system, at least a second navigation element configured to produce a second virtual image that represents an orientation of the opening in the sidewall exposing the element relative to the housing.

8. The surgical device of claim 7, where the side wall is flexible to conform to soft tissue to form a seal against the tissue upon application of a vacuum from the vacuum source so that the vacuum pulls tissue within the opening causing the tissue to contact the tissue heating element such that the tissue heating element is offset from the opening.

9. The surgical device of claim 7, where a portion of the elongate member adjacent to the tissue heating element is flexible to accommodate bending around the soft tissue of organs and to accommodate conformation to the soft tissue.

* * * * *